(12) United States Patent
Nakao et al.

(10) Patent No.: US 9,041,921 B2
(45) Date of Patent: May 26, 2015

(54) DEFECT INSPECTION DEVICE AND DEFECT INSPECTION METHOD

(75) Inventors: Toshiyuki Nakao, Yokohama (JP); Shigenobu Maruyama, Oiso (JP); Yuta Urano, Yokohama (JP); Toshifumi Honda, Yokohama (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 358 days.

(21) Appl. No.: 13/519,138

(22) PCT Filed: Jan. 17, 2011

(86) PCT No.: PCT/JP2011/000187
§ 371 (c)(1),
(2), (4) Date: Aug. 28, 2012

(87) PCT Pub. No.: WO2011/093022
PCT Pub. Date: Aug. 4, 2011

(65) Prior Publication Data
US 2013/0003052 A1    Jan. 3, 2013

(30) Foreign Application Priority Data
Jan. 29, 2010  (JP) ................................ 2010-017620

(51) Int. Cl.
*G01N 21/00*  (2006.01)
*G01N 21/95*  (2006.01)
*G01N 21/47*  (2006.01)

(52) U.S. Cl.
CPC ............ *G01N 21/9501* (2013.01); *G01N 21/47* (2013.01)

(58) Field of Classification Search
None
See application file for complete search history.

(56) References Cited

U.S. PATENT DOCUMENTS

| 5,903,342 | A | 5/1999 | Yatsugake et al. |
| 7,710,557 | B2 * | 5/2010 | Oshima et al. ............ 356/237.5 |
| 2004/0156042 | A1 | 8/2004 | Vaez-Iravani et al. |
| 2007/0182958 | A1 | 8/2007 | Manabe et al. |
| 2008/0304055 | A1 | 12/2008 | Oshima et al. |

FOREIGN PATENT DOCUMENTS

| JP | 9-304289 | 11/1997 |
| JP | 2000-162141 | 6/2000 |
| JP | 2005-517906 | 6/2005 |
| JP | 2007-240512 | 9/2007 |
| JP | 2008-268140 | 11/2008 |
| JP | 2009-276273 | 11/2009 |

* cited by examiner

*Primary Examiner* — Kara E Geisel
*Assistant Examiner* — Amanda Merlino
(74) *Attorney, Agent, or Firm* — Baker Botts L.L.P.

(57) ABSTRACT

A defect inspection device has: an illumination optical system which irradiates a predetermined region of an inspection target with illumination light; a detection optical system which has a detector provided with a plurality of pixels by which scattered light from the predetermined region of the inspection target due to illumination light from the illumination optical system can be detected; and a signal processing portion which is provided with a correction portion which corrects pixel displacement caused by change in a direction perpendicular to a surface of the inspection target with respect to a detection signal based on the scattered light detected by the detector of the detection optical system, and a defect determination portion which determines a defect on the surface of the inspection target based on the detection signal corrected by the correction portion.

6 Claims, 15 Drawing Sheets

DIRECTION OF PIXEL DISPLACEMENT: NEGATIVE (−: MINUS)
MAGNITUDE OF PIXEL DISPLACEMENT: LENGTH OF LINE SEGMENT OA

DEFECT MAP         Haze MAP

DEFECT INSPECTION DEVICE AND DEFECT INSPECTION METHOD

TECHNICAL FIELD

The present invention relates to a defect inspection device and a defect inspection method for inspecting each defect on a sample surface.

BACKGROUND ART

In a production line of a semiconductor substrate, a thin-film substrate, etc., inspection of defects on a surface of the semiconductor substrate, the thin-film substrate, etc. is performed in order to keep and improve the yield rate of products. As the background art, there is a method of "irradiating a wafer surface with a laser beam condensed into a size of tens of micrometers, condensing and detecting scattered light generated from each defect, and detecting each defect having a size of from the order of tens of nanometers to the order of micrometers or more". Patent Literature 1 (JP-A-9-304289) and Patent Literature 2 (JP-A-2000-162141) have been known as the background art.

In Patent Literature 3 (JP-A-2008-268140), there has been disclosed a method of "illuminating one and the same defect several times in one inspection with an illuminating optical system for performing linear illumination and a detecting optical system for performing detection while splitting an illumination-target region by a line sensor, and adding the scattered light to thereby improve the detection sensitivity".

As a method for reducing a detection error caused by change in height of a wafer during inspection, in Patent Literature 4 (JP-A-2007-240512), there has been disclosed a method of "illuminating a surface of a rotating wafer with a beam emitted from a first light source to form a beam spot, detecting scattered light caused by a defect such as a foreign matter on the wafer surface in a plurality of detections to output signals, detecting vertical motion of the wafer surface by using white light or broadband light from a second light source, correcting the position of the beam spot on the wafer surface based on information of the vertical motion of the wafer surface to suppress coordinate error caused by the vertical motion of the wafer surface, correcting the direction and position of emission of light from the first light source to suppress coordinate error caused by change in the first light source to thereby improve coordinate accuracy of the defect such as a foreign matter to be detected, further correcting the diameter of the illuminating beam spot to suppress an individual difference in detection sensitivity or foreign matter coordinate detection error between devices".

CITATION LIST

Patent Literatures

Patent Literature 1: JP-A-9-304289
Patent Literature 2: JP-A-2000-162141
Patent Literature 3: JP-A-2008-268140
Patent Literature 4: JP-A-2007-240512

SUMMARY OF THE INVENTION

Technical Problem

With the recent rapid advance of miniaturization of LSI wiring, the size of a defect to be detected has come close to a detection limit of optical inspection. According to a semiconductor roadmap, mass production of 36 nm-node LSI's will start at 2012, so that an unpatterned sample inspection device needs to have capability of detecting a defect with the same size as a half pitch of DRAM. The defect is a particle deposited on a sample as a target of inspection, a crystal originated particle (COP), a scratch generated by polishing, etc.

It has been known that the size I of scattered light generated when a defect is illuminated with a laser has the relation $I \propto D^6$ in which D is the particle diameter of the defect. That is, because the scattered light generated thus decreases rapidly as the defect size decreases, it is necessary to increase scattered light generated from a fine defect.

Although increase of a laser output is a method of increasing scattered light generated from a defect, the method has a possibility that surface temperature of a laser irradiation portion on a sample will increase to cause damage to the sample. Although elongation of irradiation time can intensify scattered light to be detected, the inspectable area per unit time is reduced to thereby bring lowering of throughput.

For following the semiconductor miniaturization, it is necessary to improve detection sensitivity of the inspection device intermittently. In Patent Literature 1 and Patent Literature 2, increase of laser power can improve detection sensitivity but there is a possibility that the sample will be damaged. Although elongation of irradiation time may improve detection sensitivity, the inspectable area per unit time is reduced to thereby bring lowering of throughput.

To improve detection sensitivity while avoiding damage to the sample and keeping the throughput, it is necessary to increase the signal amplification effect based on signal addition. As a method of making it possible to detect a finer defect without causing damage to the sample and lowering of the throughput, a method (Patent Literature 3) of detecting a predetermined region (one defect) several times and adding resulting signals has been conceived.

However, because the sample rotates at a high speed of several thousand RPM (Rotation Per Minute) during inspection, change in height of the sample per se in a direction perpendicular to the sample is caused by vibration or convection. In this case, a region on the sample to be subjected to laser irradiation is displaced from a region actually subjected to laser irradiation so that an image of scattered light is formed on a position displaced from the original position of a line sensor. Accordingly, the image of the scattered light may be formed on a pixel position of the line sensor different from the predetermined pixel or may be formed as a blurred image because of defocusing. When a plurality of image-forming optical systems are disposed in directions with respect to the sample surface, pixels for detecting scattered light substantially from one and the same region are associated with each other by adjustment at shipping so that signal addition processing is performed based on the correspondence between pixels. That is, there occurs a problem that the correspondence between pixels detecting scattered light substantially from one and the same region is collapsed by change in sample height during inspection so that signals of one and the same region cannot be added up (this problem will be hereinafter referred to as "detection pixel displacement" or "pixel displacement" simply).

When a line sensor is used, the case where scattered light from one defect is detected by a plurality of pixels occurs (hereinafter referred to as "pixel cracking"). In this case, the quantity of detected light is lowered and detection sensitivity is lowered.

In a method described in Patent Literature 4, correction of an illumination position in accordance with change in wafer height has been disclosed. When an image-forming optical system is used, it is however necessary not only to correct the illumination position but also to correct the distance between the wafer and the image-forming optical system. This method cannot avoid detection pixel displacement caused by change in wafer height.

An object of the invention is to provide a defect inspection device and a defect inspection method for avoiding the influence of detection pixel displacement to make it possible to add up scattered light generated substantially from one and the same region.

Solution to Problem

The summary of the representative one s of the inventions disclosed in this application will be explained briefly as follows.

(1) A defect inspection device including: an illumination optical system which irradiates a predetermined region of an inspection target with illumination light; a detection optical system which has a detector provided with a plurality of pixels by which scattered light from the surface of the inspection target due to illumination light from the illumination optical system can be detected; a correction portion which corrects pixel displacement caused by change in a direction perpendicular to a surface of the inspection target with respect to a detection signal based on scattered light detected by the detector of the detection optical system, and a detection portion which detects a defect on the surface of the inspection target based on the detection signal corrected by the correction portion.

(2) In the defect inspection device described in (1), a plurality of detectors are provided in the detection optical system so that the detectors can detect scattered light from the surface of the inspection target in different azimuth angle directions with respect to the surface of the inspection target, respectively; and the correction portion corrects the pixel displacement with respect to a plurality of detection signals based on scattered light detected by the plurality of detectors respectively, wherein the device further includes an adding portion which adds the plurality of detection signals corrected by the correction portion.

Advantageous Effects of Invention

According to the invention, it is possible to provide a defect inspection device and a defect inspection method which can inspect each fine defect on a sample surface.

DESCRIPTION OF EMBODIMENTS

Figure 1:
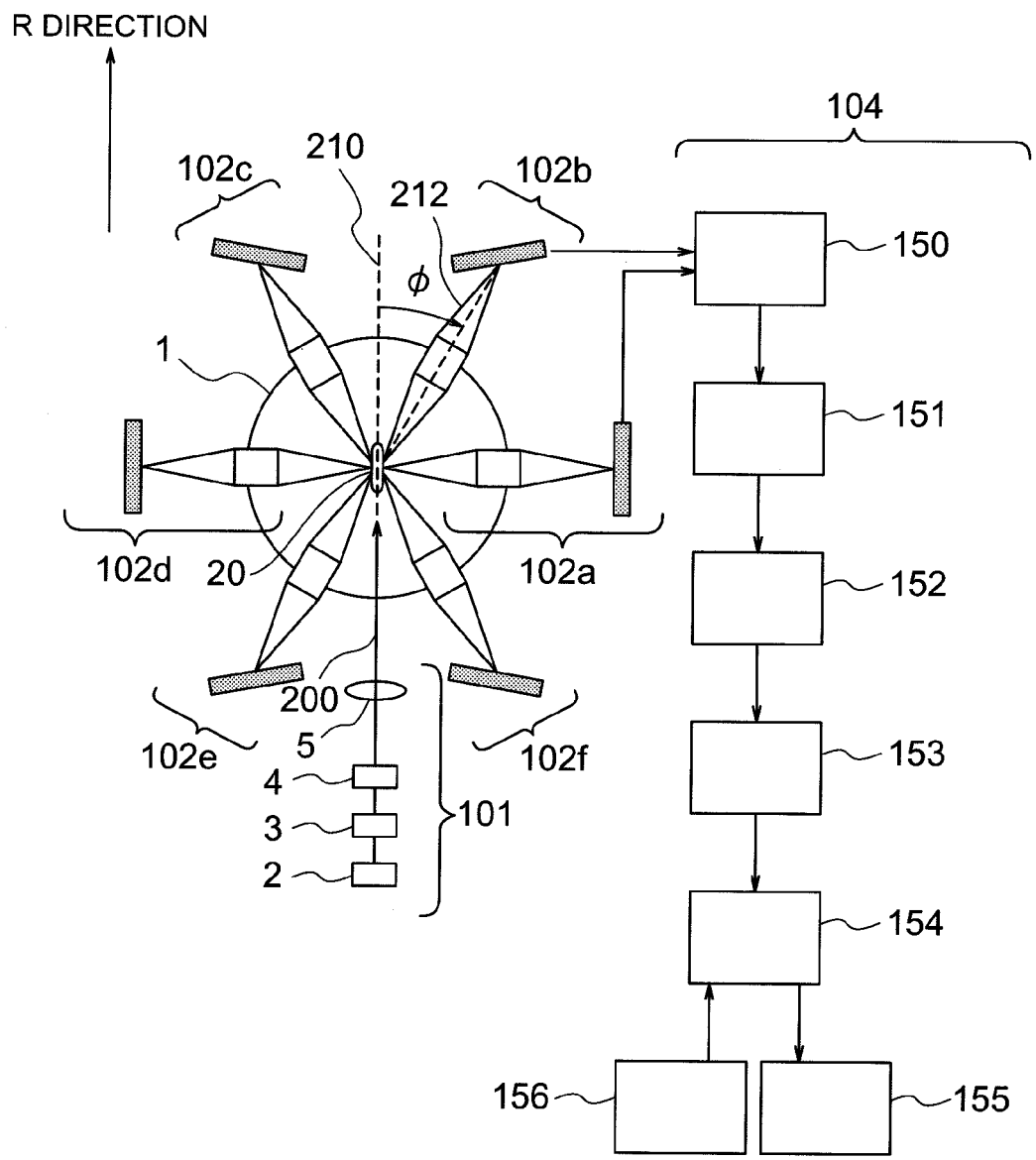
FIG. 1 is a top view of a first embodiment of a defect inspection device according to the invention.
Figure 2:
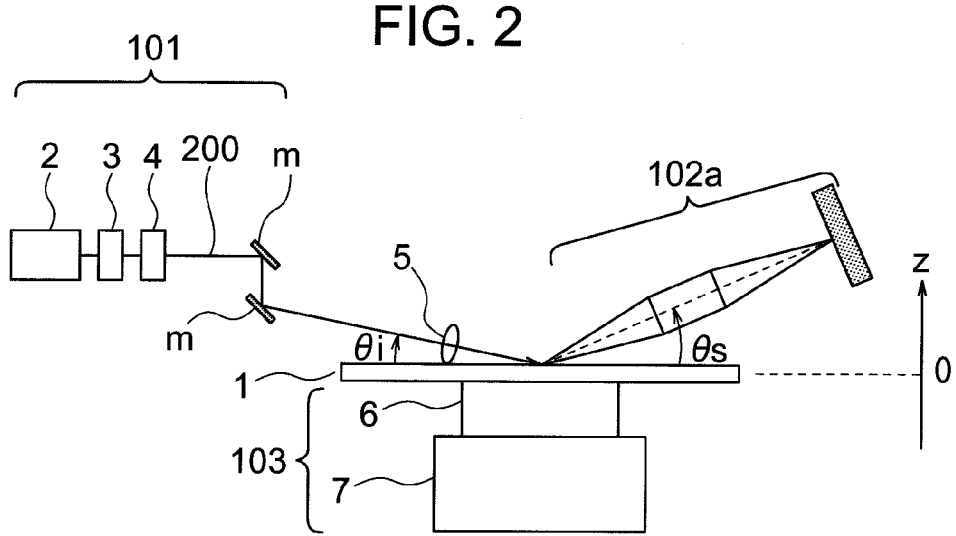
FIG. 2 is a side view of the first embodiment of the defect inspection device according to the invention.

An embodiment of a defect inspection device according to the invention will be described with reference to FIGS. 1 and 2 by way of example. The defect inspection device shown in FIGS. 1 and 2 has an illumination optical system 101, detection optical systems 102a to 102f, a sample stage 103, and a signal processing portion 104. FIG. 1 is a plan view (top view) of the inspection device. FIG. 2 is a side view of the illumination optical system 101, the detection optical system 102a and the sample stage 103.

The illumination optical system 101 has a laser light source 2, a beam expander 3, a polarizing element 4, mirrors m, and a condensing lens 5. The beam diameter of a laser beam 200 emitted from the laser light source 2 is adjusted to a desired size by the beam expander 3. The laser beam 200 is then converted into a desired polarized state by the polarizing element 4 and irradiated at an elevation angle θi on an inspection-target region of a sample 1 by the condensing lens 5 through the reflection mirrors m.

Here, the laser light source 2 is a laser light source which oscillates a laser beam with a wavelength of 355 nm, and the illumination elevation angle θi is an angle of 10 degrees from the sample surface. An illumination region 20 is substantially shaped like an ellipse on the sample surface and has a size of about 1000 μm in the major axis direction and about 20 μm in the minor axis direction.

The beam expander 3 is an anamorphic optical system constituted by a plurality of prisms. The beam expander 3 changes the beam diameter in only one direction in a plane perpendicular to the optical axis so that the sample 1 is subjected to spot illumination or linear illumination by the condensing lens 5.

The detection optical systems 102a to 102f are arranged in directions of different azimuth angles φ and detect scattered light generated from the illumination region 20 on the sample. The detection optical systems 102a to 102f are arranged at intervals of about 60 degrees in terms of the directions of azimuth angles. The azimuth angles φ at which the detection optical systems 102a to 102f are arranged are 30, 90, 150, 210, 270 and 330 degrees respectively.

The detection optical system 102a is arranged in the direction of an elevation angle θs with respect to the sample surface. The detection elevation angle θs is an angle of 30 degrees with respect to the sample surface. The numerical aperture is 0.3. The same rule is applied to the detection optical systems 102b to 102f. Each of the detection optical systems 102b to 102f is arranged at the detection elevation angle of 30 degrees with respect to the sample surface, and the numerical aperture is 0.3.

Figure 3:
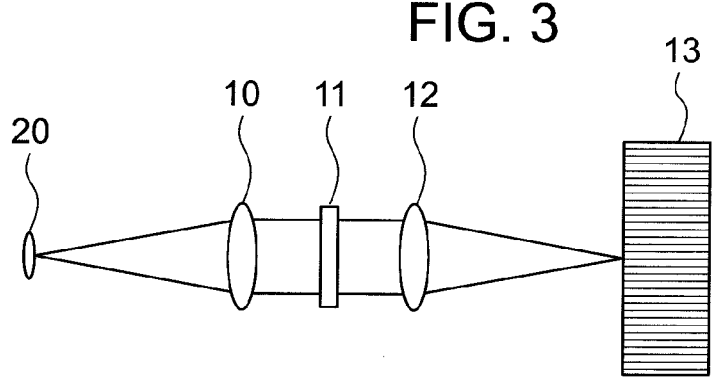
FIG. 3 shows a detection optical system in the first embodiment of the defect inspection device according to the invention.

The detection optical systems 102a to 102f have substantially the same configuration. Details of the configuration of each of the detection optical systems 102a to 102f are shown in FIG. 3. Each of the detection optical systems 102a to 102f has an objective lens 10, a polarizing element 11, an image-forming lens 12, and a line sensor (detector) 13. The objective lens 10 is a reducing system having an optical magnification of 0.1.

For example, the polarizing element 11 is a polarizing filter, a PBS (Polarized Beam Splitter) or the like. The polarizing element 11 reduces scattered light (referred to as "roughness scattered light") generated from fine roughnesses of the sample surface by polarization detection so that finer defects can be detected. The polarizing element 11 can rotate around the optical axis of the detection optical system and can be detached and attached. NSPFU-30C made by SIGMA KOKI Co., Ltd. may be used as the polarizing filter. PBSW-10-350 etc. made by SIGMA KOKI Co., Ltd. may be used as the PBS.

The line sensor 13 can detect scattered light with respect to a plurality of pixels. 25S3923256Q etc. made by Hamamatsu Photonics K.K. may be used as the line sensor 13. The number of pixels of 25S3924-256Q is 256, the pixel pitch thereof is 25 μm, and the pixel height thereof is 0.5 mm.

Figure 4:
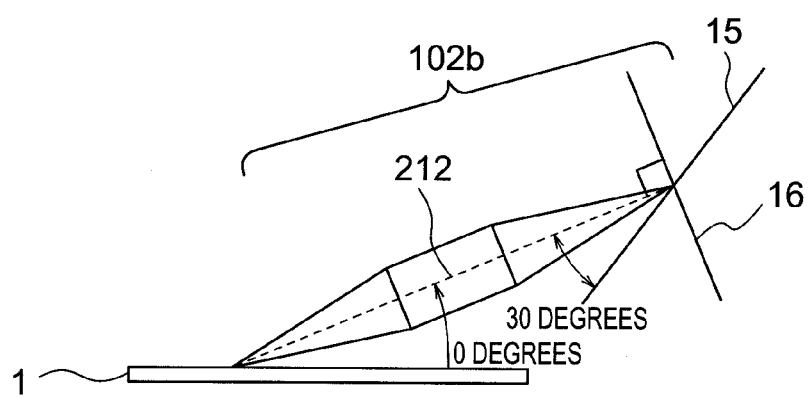
FIG. 4 is a side view of the detection optical system in the first embodiment of the defect inspection device according to the invention.

The illumination region 20 and the line sensor 13 have a conjugate position relation, so that an image of scattered light from the illumination region 20 is formed on each of pixels of the line sensor 13. When the line sensors of the detection optical systems 102a and 102d are arranged so as to be substantially parallel with a longitudinal direction 210 of the illumination region 20, the line sensors and the illumination region 20 have a conjugate position relation. Because the detection optical system 102b is arranged in a direction with an azimuth angle of 30 degrees and an elevation angle of 30 degrees, an image is formed on an image surface 15 inclined at 30 degrees with respect to the optical axis as shown in FIG. 4 when image formation is performed in the condition of an optical magnification of 1. To correct the inclination of the image and form an image on a surface substantially perpendicular to an optical axis 212, the detection optical system may be provided as a reducing system having a magnification. Because the objective lens 10 is a reducing system having an optical magnification of 0.1, the inclination of the image is corrected so that an image is formed on an image plane 16 substantially perpendicular to the optical axis 212. The total optical magnification is determined based on the magnification of each image-forming lens 12, so that the total optical magnification of the detection optical systems 102a to 102f is 10.

Figure 5:
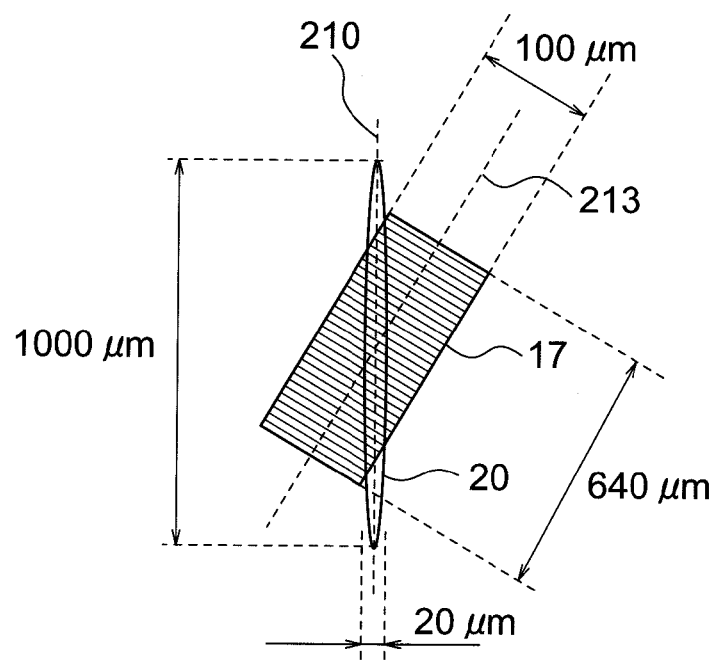
FIG. 5 is a view for explaining the spatial position relation between an illumination region and a line sensor and the position relation between the illumination region and the line sensor with respect to a detection range on a sample surface.

When the line sensor 13 of the detection optical system 102b is arranged in the plane 16 perpendicular to the optical axis and in a position parallel to the sample 1, the illumination region 20 on the surface of the sample 1 and a detection range 17 of the line sensor 13 have a position relation as shown in FIG. 5, so that an angle of 30 degrees is formed between the longitudinal direction 210 of the illumination region 20 and a direction 213 of arrangement of pixels of the line sensor. In this state, it is necessary to rotate the line sensor around the optical axis 212 because all scattered light generated from the illumination region 20 cannot be supplemented. The angle between the longitudinal direction 210 of the illumination region 20 and the direction 213 of arrangement of the pixels of the line sensor is 30 degrees. Therefore, when the line sensor is rotated by the same angle of 30 degrees, the angle between the longitudinal direction 210 of the illumination region 20 and the direction 213 of arrangement of the pixels of the line sensor can be about 0 degrees so that all scattered light generated from the illumination region 20 can be supplemented and an image can be formed on the line sensor. With respect to the detection optical systems 102b, 102c, 102e and 102f, the angle between the longitudinal direction 210 of the illumination region 20 and the direction 213 of arrangement of the pixels of the line sensor varies according to the detection azimuth angle. Therefore, each line sensor is rotated around the optical axis in accordance with the detection azimuth angle so that all scattered light generated from the illumination region 20 is supplemented and an image is formed on the line sensor.

The sample stage 103 in FIG. 2 includes a chuck (not shown) for holding the sample 1, a Z stage (not shown) for performing height control, a rotation stage 6 for rotating the sample, and a translation stage 7 for moving the sample 1 in an R direction. The sample stage 103 performs rotational scanning and translational scanning to thereby scan the illumination region 20 so that the whole surface of the sample 1 is illuminated spirally. Here, the height of the sample surface in a stationary state is defined as z=0 and the vertically upward direction is defined as a positive direction.

The signal processing portion 104 in FIG. 1 is provided with an analog circuit 150, an A/D conversion portion 151, an adjacent pixel integration portion (pixel displacement correction portion) 152, a signal addition/defect determination portion 153, a CPU 154, a map output portion 155, and an input portion 156.

The reason why pixel displacement occurs based on change in sample height will be described below with reference to FIGS. 6 and 7.

Figure 6:
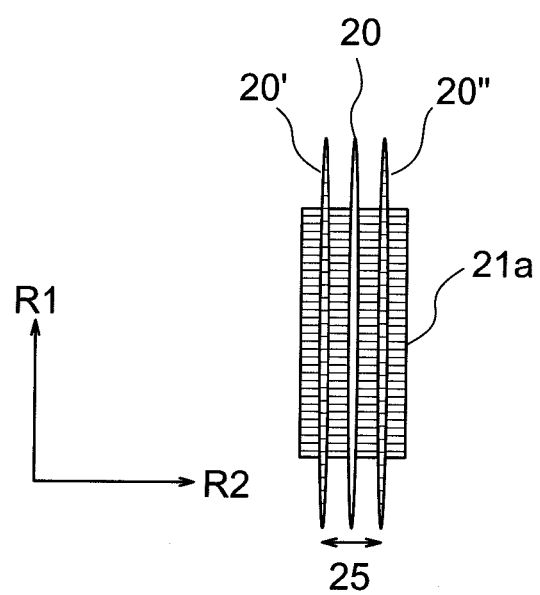
FIG. 6 is a view for explaining the position relation between the illumination region and the detection range on the sample surface.

FIG. 6 shows the position relation between a detection range 21a of the line sensor and the illumination region 20 on the surface of the sample 1 viewed from a detection azimuth angle at which the detection optical system 102a is arranged. FIG. 7 shows the position relation between a detection range 21b of the line sensor and the illumination region 20 on the surface of the sample 1 viewed from a detection azimuth angle at which the detection optical system 102b is arranged. Here, the direction of arrangement of the pixels of the line sensor is defined as R1, and the direction of height of the pixels is defined as R2. R1 and R2 cross each other at right angles.

Figure 7:
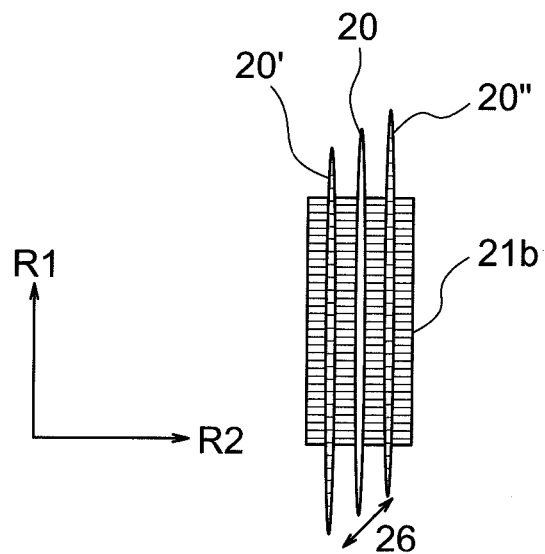
FIG. 7 is a view for explaining the position relation between the illumination region and the detection range on the sample surface.

When there is no change in sample height, the position relation between the illumination region 20 and the detection range 21a in FIG. 6 and the position relation between the illumination region 20 and the detection range 21b in FIG. 7 are the same. In this state, the detection ranges of the two line sensors are initially adjusted to be substantially one and the same region. That is, correspondence of pixels for detecting scattered light substantially generated from one and the same region is determined in the initial adjustment, so that scattered light signals may be added in accordance with the correspondence during inspection.

The case where change in sample height occurs will be described next. When the height of the sample surface is a height of z=0, the illumination region 20 and the line sensor 13 are adjusted in focus. However, when the height of the sample surface changes, the position where an image of scattered light generated from the illumination region 20 is formed on the line sensor changes because the illumination region 20 and the line sensor 13 are out of focus. Assume that "h" is an arbitrary constant. It is shown that the illumination region 20 is displaced to the position of an illumination region 20' when the height of the sample surface is shifted by +h µm in a z direction because the sample 1 rotates at a high speed, and that the illumination region 20 is displaced to the position of an illumination region 20" when the height of the sample surface is shifted by −h µm in the z direction because the sample 1 rotates at a high speed.

In the example of FIG. 6, a direction 25 of displacement of the illumination region 20 is only one direction parallel to the pixel height direction R2. In this case, there is no occurrence of pixel displacement. On the other hand, in the example of FIG. 7, a direction 26 of displacement of the illumination region 20 is displaced not only in a direction parallel to R2 but also in a direction parallel to R1. Because the illumination region 20 is also displaced in the R1 direction, pixel displacement occurs. The correspondence of pixels set by the initial adjustment for detecting scattered light substantially generated from one and the same region is collapsed by occurrence of pixel displacement, so that the effect of signal amplification based on signal addition is reduced.

It has been known that the direction 25 or 26 of displacement of the illumination region 20 based on change in sample height varies according to the detection azimuth angle φ, and that the magnitude of displacement of the illumination region 20 varies according to the detection elevation angle θs, the detection azimuth angle φ and the magnitude of change in sample height.

Figure 8:
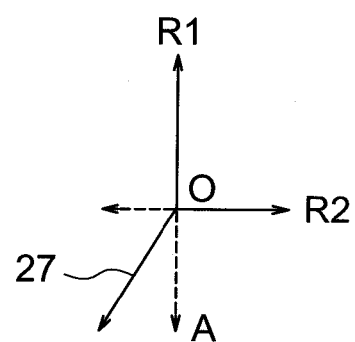
FIG. 8 is a view for explaining the position relation between the illumination region and the detection range on the sample surface.

While the direction of displacement of the illumination region 20 is hereinafter regarded as a vector decomposed into two components of R1 and R2, the sign of the R1 component is defined as the direction of pixel displacement, and the absolute value of the R1 component is defined as the magnitude of pixel displacement. On the assumption of a direction 27 of displacement of the illumination region 20 in the case of FIG. 8, the direction of pixel displacement is negative (−: minus) and the magnitude of pixel displacement is the length of a line segment OA.

In the invention, when the correspondence of pixels for detecting scattered light substantially generated from one and the same region is collapsed by occurrence of pixel displacement, signals of adjacent pixels in the line sensor are processed integrally in the following manner so that signals substantially from one and the same region can be added.

The line sensor 13 generates an electric signal in accordance with the quantity of received light. The electric signal is led into the analog circuit 150. Processing performed by the analog circuit 150 will be described below.

Figure 9:
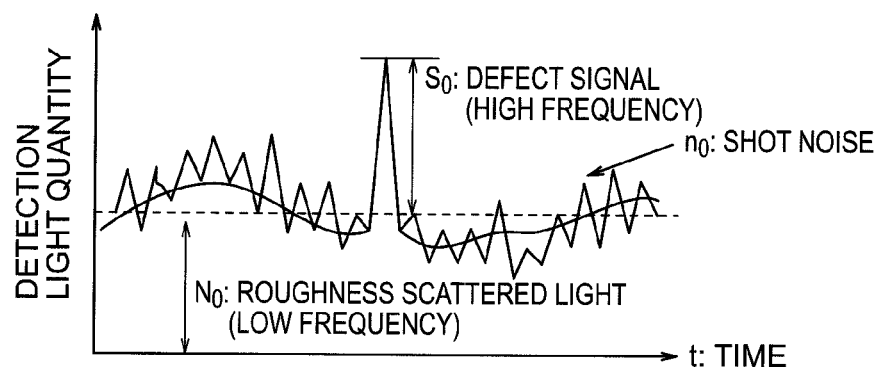
FIG. 9 is a view for explaining a detection signal.

When scattered light generated from the illumination region 20 is detected, a signal as shown in FIG. 9 is outputted from the line sensor 13. Roughness scattered light $N_0$ generated from roughnesses of the sample surface is always generated during a laser irradiation period and detected as low-frequency undulation (<the order of kHz). When roughness scattered light $N_0$ incident on the line sensor 13 is converted photoelectrically, shot noise $n_0$ is generated as random change and detected at the same time. On the other hand, defect scattered light $S_0$ generated from defects is high in frequency (>the order of kHz) compared with the roughness scattered light because the defect scattered light $S_0$ is generated in pulses only for a short period when the illumination region 20 with an illumination width of 20 µm passes through each position where a defect is located. That is, when the detection signal shown in FIG. 9 is led into the analog circuit 150, a high-pass filter (pass band: >the order of kHz) is applied to the detection signal to thereby make it possible to extract a defect signal and a low-pass filter (pass band: <the order of kHz) is applied to the detection signal to thereby make it possible to extract the intensity of roughness scattered light (hereinafter referred to as Haze signal).

From the above description, the high-pass filter is applied to the electric signal generated based on the defect scattered light detected by the line sensor 13 while the low-pass filter is applied to the electric signal generated based on the roughness scattered light detected by the line sensor 13. Consequently, the defect signal and the Haze signal can be processed separately.

The signals subjected to the aforementioned filtering processes are converted into digital signals at a sampling pitch not lower than the order of MHz by the A/D conversion portion 151. The defect signal converted into the digital signal is led into the adjacent pixel integration portion (pixel displacement correction portion) 152 in which signals of adjacent pixels are integrated (pixel displacement is corrected).

Figure 10:
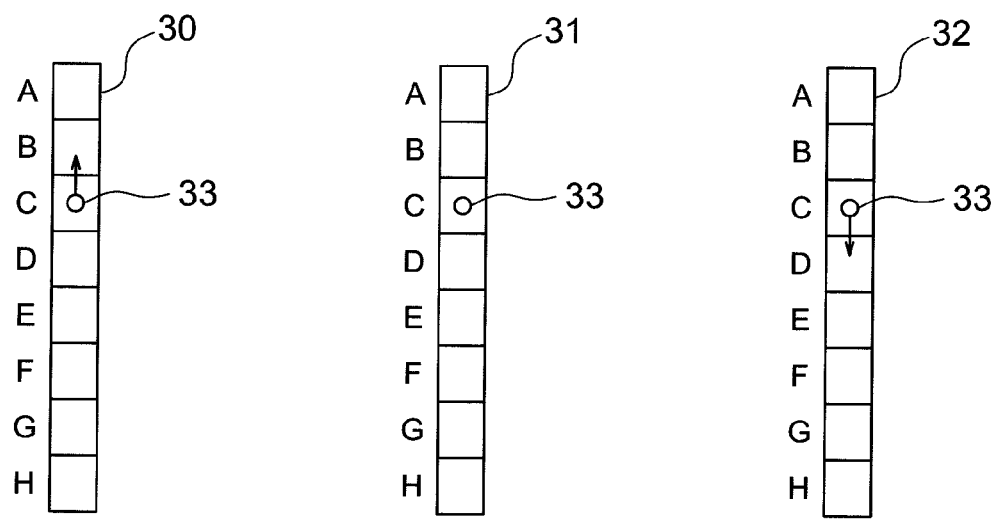
FIG. 10 is a view showing the relation between each line sensor and the position where an image of defect scattered light is formed.

A method of signal integration will be described with reference to FIG. 10. FIG. 10 shows the position relation between pixels of the line sensor 13 and a pixel on which an image of defect scattered light 33 is formed. The case where an image of defect scattered light 33 is formed substantially in the center of a pixel C in each line sensor when there is no occurrence of change in sample height will be described by way of example while eight pixels (A to H) in each of the line sensors 30, 31 and 32 used in the detection optical systems 102f, 102a and 102b respectively are taken up as a subject for discussion.

(1) In a state where change in sample height does not occur or is too small to cause pixel displacement, detection signals of the pixels C in all the line sensors may be added up.

(2) When pixel displacement of about one pixel occurs in the case where change in sample height occurs in the +z direction, defect scattered light 33 is still detected by the pixel C of the line sensor 31 but defect scattered light 33 is detected by the pixel B of the line sensor 30 and detected by the pixel D of the line sensor 32. That is, detection signals of the pixel B in the line sensor 30, the pixel C in the line sensor 31 and the pixel D in the line sensor 32 may be added up.

Figure 11:
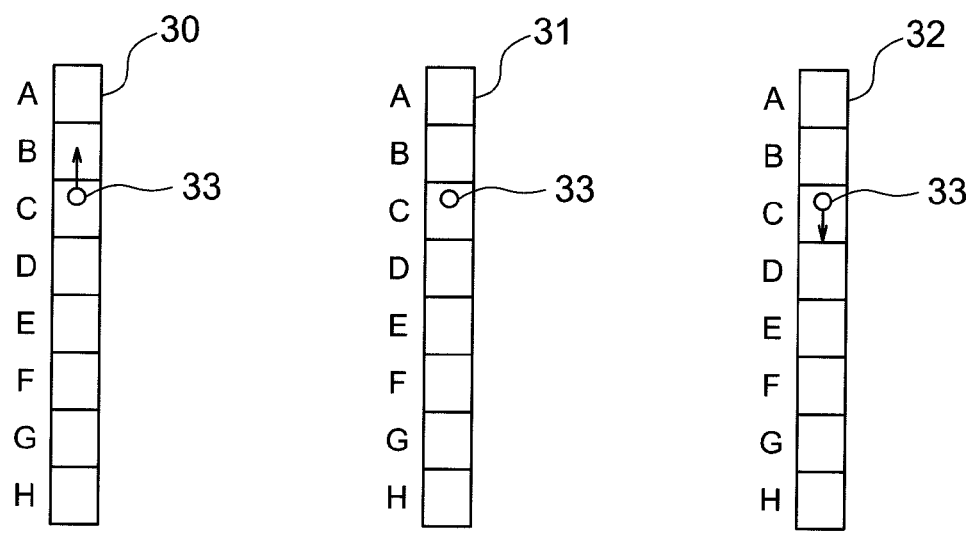
FIG. 11 is a view showing the relation between each line sensor and the position where an image of defect scattered light is formed.

(3) In a state where an image of defect scattered light is formed substantially in the center of the pixel C, detection signals substantially from one and the same region can be detected in spite of occurrence of change in sample height as long as output signals of the respective line sensors are subjected to the aforementioned process (1) or (2) by parallel processing. However, a case where an image of defect scattered light is formed out of the center of the pixel may be conceived. In addition, a case where the magnitude of pixel displacement is not larger than one pixel may be conceived. The case shown in FIG. 11 is therefore assumed. In the line sensor 31, pixel displacement does not occur but an image of defect scattered light 33 is formed in a place out of the center of the pixel. Because the magnitude of pixel displacement is not larger than one pixel, pixel displacement occurs in the line sensor 30 so that an image of defect scattered light is detected by the pixel B of the line sensor 30, but pixel displacement does not occur in the line sensor 32 so that an image of defect scattered light is detected by the pixel C of the line sensor 32.

In this case, signals substantially from one and the same region cannot be added up only by the aforementioned processes (1) and (2).

(4) In the case of (3), detection signals of adjacent pixels may be subjected to an integration process. In the line sensor 30, detection signals of the pixels B and C are integrated so that detection signals of two pixels are processed as one detection signal. In the line sensor 32, detection signals of the pixels C and D are processed integrally. In the line sensor 31, detection signals of the pixels B, C and D are processed integrally. Incidentally, integration is performed while the detection signals of the pixels B and D are multiplied by a weight of 0.5. By integrally processing signals of adjacent pixels in this manner, scattered light substantially from one and the same region can be added up in all the cases of (1) to (3).

(5) The case where the magnitude of pixel displacement is not smaller than two pixels may be conceived. In this case, the combination of pixels to be integrated may be changed. In the line sensor 30, detection signals of the pixels A and B are integrated. In the line sensor 32, detection signals of the pixels D and E are integrated. In the line sensor 31, the same integration as (4) may be performed. Because the combination of pixels to be integrated is changed in accordance with the magnitude of pixel displacement as described above, patterns of the quantity of change of pixel displacement are prepared while the magnitudes of change in sample height allowed to be generated in accordance with the performance of the inspection device are grasped or the magnitudes of change in sample height are really measured with a sensor to thereby determine the quantity of change of pixel displacement so that the influence of pixel displacement can be avoided when the quantity of change of pixel displacement is calculated by parallel processing. When patterns of the quantity of change of pixel displacement are prepared, detection signals corresponding to the patterns respectively are subjected to an integration process and, for example, a pattern having the highest SN is selected so that the optimum quantity of pixel displacement can be determined.

(6) Although the items (1) to (5) have been described in the case where the sample height changes in the +z direction, there may be the case where the sample height changes in the −z direction. In this case, the combination of pixels to be integrated may be changed because pixel displacement occurs in the opposite direction. For example, when the sample height changes in the −z direction so that pixel displacement by about one pixel occurs, detection signals of the pixels C and D in the line sensor 30 may be integrated and detection signals of the pixels B and C in the line sensor 32 may be integrated. The line sensor 31 may be processed in the same manner as (4).

(7) As described above, integration processes are performed with a plurality of combinations and threshold processes are performed on the combinations respectively so that only signals in the case where defects are detected may be used.

(8) Although the aforementioned (1) to (7) have been described only for defect signals, the same processing is performed on Haze signals. Although description has been made on three kinds of detection signals by way of example, the aforementioned processing is performed on all detector signals.

The integrated signals are led into the signal addition/defect determination portion 153. Signals of one and the same coordinates are added up, so that defect determination, defect classification and defect size calculation due to threshold processes and Haze processing due to level determination are performed based on the sum signals.

Figure 12:
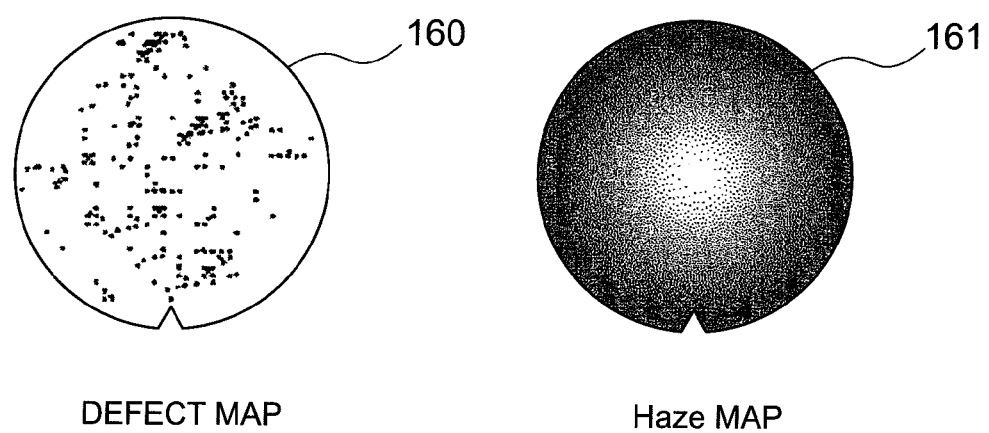
FIG. 12 is a view for explaining a defect map and a Haze map.

A defect map 160 and a Haze map 161 shown in FIG. 12 are displayed by the map output portion 155 through the CPU 154. The defect map 160 is displayed based on defect type, defect size and detection coordinates fetched at inspection time. The Haze map 161 is displayed based on Haze signal level and detection coordinates fetched at inspection time. The input portion 156 includes a user interface through which a user can perform recipe setting etc.

The advantages of presence of detection optical systems at a plurality of azimuth angles are not only in that the signal amplification effect based on signal addition can be increased but also in that defect detection sensitivity can be improved when detection optical systems to be used are selected or detection signals in the respective detection optical systems are used while weighted. The roughness scattered light has azimuth angle dependence which depends on the roughness state of the sample surface. For example, a sample such as Si having a very smooth surface in terms of surface roughness has a tendency to generate roughness scattered light intensively in a direction of incidence of the laser beam 200, that is, in a direction of the azimuth angle at which each of the detection optical systems 102e and 102f is located. A sample such an Al deposition film having a large surface roughness has a property to generate roughness scattered light intensively in a direction of movement of the laser beam 200, that is, in a direction of the azimuth angle at which each of the detection optical systems 102b and 102c is located. When only detection signals detected by defect detection optical systems located at azimuth angles for generating roughness scattered light weakly are used or processing is performed in such a manner that weights corresponding to the magnitudes of roughness scattered light are multiplied as gains by the detection signals, defect detection sensitivity can be improved.

Although laser illumination is performed in a direction parallel to the longitudinal direction 210 of illumination in FIG. 1, the direction of laser irradiation need not be substantially the same as the longitudinal direction 210 of illumination, that is, illumination may be performed in different azimuth angle directions. The advantage of illumination in different directions is in that classification performance of defects having directivities in terms of defect shape such as scratches can be improved. Scattered light generated from a defect such as COP substantially symmetric with respect to the azimuth angle direction does not have azimuth angle dependence but has a tendency to be generated substantially evenly in all azimuth angle directions. On the other hand, scattered light generated from a defect such as a scratch asymmetric with respect to the azimuth angle direction has azimuth angle dependence. Moreover, because the azimuth angle characteristic of scattered light generated from a scratch depends on an azimuth angle of incidence of illumination, defect classification accuracy and size calculation accuracy can be improved when the direction of illumination is changed actively and signals of detection systems located in respective azimuth angle directions are compared.

Figure 13:
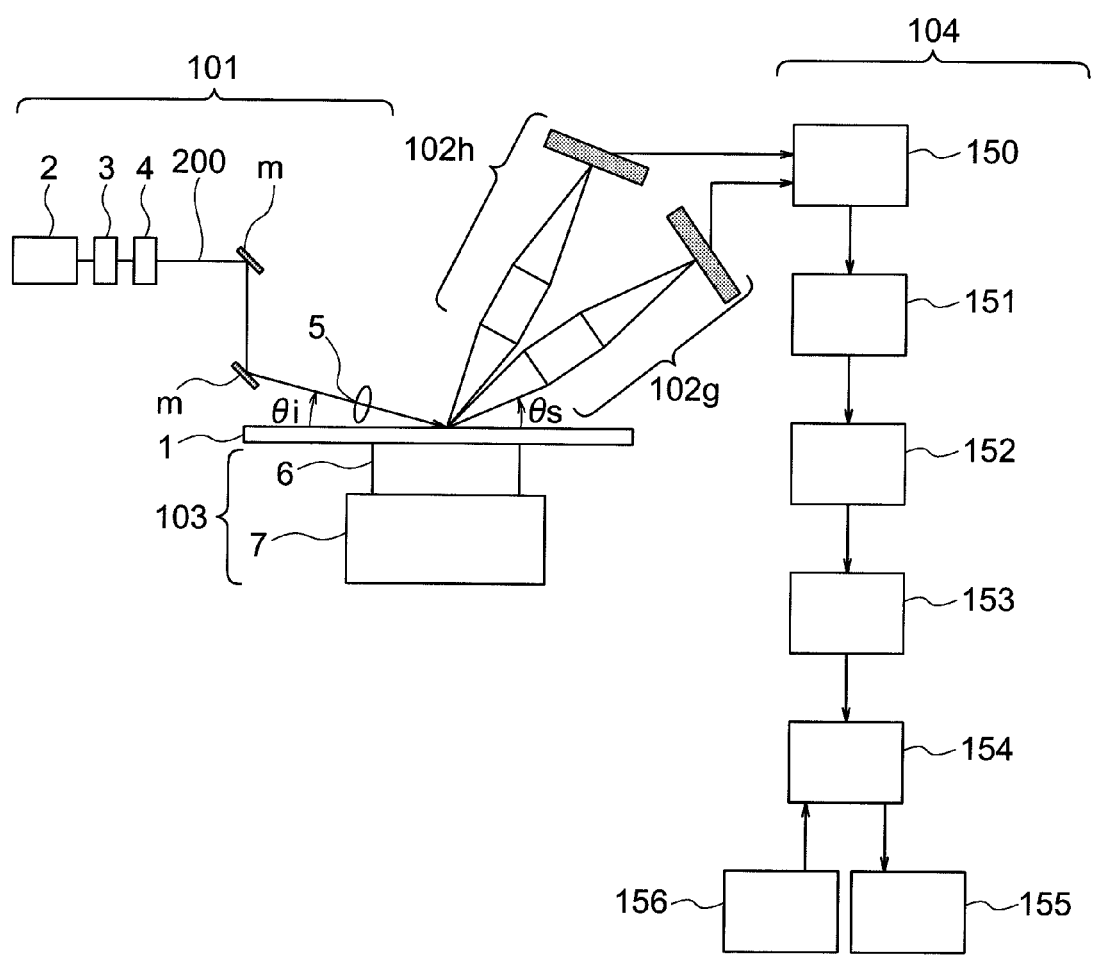
FIG. 13 is a view of the first embodiment of the defect inspection device according to the invention.

FIG. 13 is an example of a side view of the embodiment shown in FIG. 1. An oblique illumination optical system 101 for performing illumination at a low elevation angle θi, a low angle detection optical system 102g for performing scattered light detection in a low elevation angle direction θs and a detection optical system 102h for performing detection at a higher elevation angle than that of the low angle detection optical system are provided in FIG. 13.

The illumination elevation angle θi of the oblique illumination optical system 101 is 10 degrees with respect to the sample surface. As an oblique illumination optical system, a perpendicular illumination optical system for illuminating the sample substantially in a perpendicular direction may be provided (not shown).

The elevation angle at which the low angle detection optical system 102g is arranged is 30 degrees whereas the elevation angle at which the high angle detection optical system 102h is arranged is 60 degrees. Both the numerical aperture of the low angle detection optical system 102g and the numerical aperture of the high angle detection optical system 102h are 0.3.

The detection signals are inputted to the analog circuit 150, separated into defect signals and Haze signals by the high-pass filter and the low-pass filter and converted into digital signals at a sampling pitch of the order of MHz or higher by the A/D conversion portion 151. The digital signals generated by the conversion are led into the adjacent pixel integration portion (pixel displacement correction portion) 152 and corrected based on set combinations (patterns) of the quantity of change of pixel displacement. The correction results are subjected to threshold processing or the like so that, for example, a pattern having the highest S/N as a result is selected. The detection signals are integrated based on the quantity of change of pixel displacement (pixel displacement quantity) of the selected pattern. In the integrated signals, signals of one and the same coordinates are added up in the signal addition/defect determination portion 153. The signal addition/defect determination portion 153 performs defect determination, defect classification and defect sizing due to threshold processing and Haze processing due to level determination based on the sum signal. Then, the defect map 160 and the Haze map 161 shown in FIG. 12 are displayed by the map output portion 155 through the CPU 154. The defect map 160 is displayed based on defect signals and coordinates fetched at inspection time. The Haze map 161 is displayed based on Haze signals and coordinates fetched at inspection time. The input portion 156 includes a user interface through which a user can perform recipe setting etc.

The embodiment in which an illumination optical system and a detection optical system are located in different elevation angle directions has been described above. There are two advantages as follows.

When a particle deposited on the sample is illuminated by the oblique illumination optical system, the scattering sectional area of the particle can be increased compared with the perpendicular illumination optical system. Accordingly, the quantity of scattered light generated from the particle increases so that a finer defect can be detected. Scattered light from a defect having a size of tens of nm is intensively scattered on the low elevation angle side whereas scattered light from a defect having a size of 100 nm or larger is intensively scattered on the high elevation angle side. Accordingly, when a fine defect is detected by the low elevation angle detection optical system while a relatively large defect is detected by the high elevation angle detection optical system, the range of defect size which can be detected can be enlarged.

On the other hand, with respect to a concave defect such as a COP or a scratch of the sample, the scattering sectional area of the defect can be increased to improve sensitivity for the concave defect when the defect is illuminated by the perpendicular illumination optical system. Because scattered light from the concave defect is intensively scattered on the high elevation angle side, detection sensitivity can be improved further when the high elevation angle detection optical system is used.

As described above, the intensity distribution and elevation angle characteristic of scattered light generated from each defect varies according to the defect type (particle, COP, scratch, etc.) or size. Accordingly, when signals according to illumination directions and detection directions are combined and compared, defect classification accuracy and defect size calculation accuracy can be improved.

As a method of processing respective detector signals in directions of a plurality of azimuth angles and a plurality of elevation angles, respective detection signals are added or averaged. By adding the detection signals, the quantity of detection light increases to bring an effect in improving detection sensitivity. By averaging the detection signals, the width of size which can be detected within a dynamic range of the sensor increases to bring an effect in enlarging the dynamic range.

Figure 14:
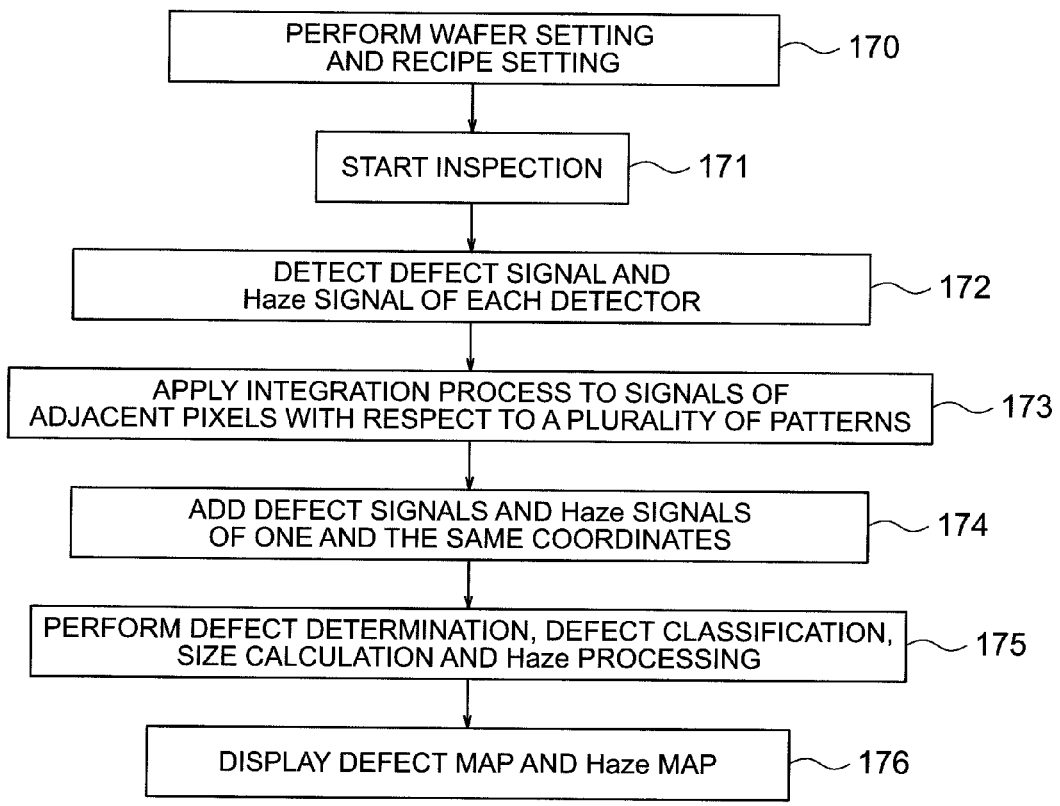
FIG. 14 is a flow of inspection in the first embodiment.

A flow of defect detection processing will be described below with reference to FIG. 14.

First, a sample 1 is set on the stage and an inspection recipe is set (step 170). Inspection is started (step 171), and a defect signal and a Haze signal are detected (step 172). With respect to signals of respective detectors, signals of adjacent pixels are subjected to integration processing (step 173). On this occasion, the detection signals are corrected based on predetermined patterns of the quantity of pixel displacement respectively and the correction results are subjected to threshold determination so that, for example, a pattern having the highest S/N as a correction result is determined as the quantity of pixel displacement. In the signal addition/defect determination portion 153, signals of one and the same coordinates are added up (step 174). Defect determination, defect classification, size calculation and Haze processing are performed based on the sum signal (step 175), so that the defect map and the Haze map are displayed (step 176).

Although description has been made in the case where the laser light source 2 is a light source which oscillates a wavelength of 355 nm, the laser light source 2 may be a laser light source which oscillates a visible, ultraviolet or vacuum ultraviolet laser beam.

Although description has been made in the case where the illumination region 20 is substantially shaped like an ellipse on the sample surface and has a size of about 1000 μm in the major axis direction and about 20 μm in the minor axis direction by way of example, the illumination region 20 need not be shaped like an ellipse and the size of the illumination region 20 is not limited.

Although the embodiment in which six detection optical systems are located in different azimuth angle directions φ has been described with reference to FIG. 1, the number of detection optical systems need not be limited to six. The detection azimuth angle φ and the detection elevation angle θs are not limited.

Although description has been made in the case where the objective lens 10 has an optical magnification of 0.1 by way of example, the magnification is not limited. Although description has been made in the case where the total optical magnification of the detection optical systems 102a to 102f is 10 by way of example, the total optical magnification is not limited.

The numerical apertures of the detection optical systems 102a to 102f need not be all substantially the same or need not be different from one another.

Although description has been made in the case where the illumination optical system 101 performs illumination by the combination of the expander 3 and the condensing lens 5 by way of example, a cylindrical lens may be used for linear illumination. When a cylindrical lens is used singly, linear illumination can be applied on the sample without use of any anamorphic optical system for changing the beam diameter in only one direction in a plane perpendicular to the optical axis. Accordingly, the beam expander 3 can be dispensed with, so as to be effective in making the optical system slimmer.

The line sensor 13 is used for receiving scattered light and performing photoelectric conversion. A multi-anode photomultiplier tube, a TV camera, a CCD camera, a photodiode, a linear sensor or a highly sensitive image sensor etc. obtained by combining an image intensifier with these may be used as the line sensor 13. For example, use of a two-dimensional sensor permits a wide region to be inspected at a time.

Although description has been made in the case where the line sensor has 256 pixels with a pixel size of 25 μm, the number of pixels and the pixel size are not limited.

A plurality of low angle detection optical systems $102g$ and a plurality of high angle detection optical systems $102h$ are located in different azimuth angle directions $\phi$, and the elevation angles at which these detection optical systems $102g$ and $102h$ are arranged need not be all substantially the same or need not be different from one another.

The numerical apertures of the low angle detection optical systems $102g$ and the high angle detection optical systems $102h$ need not be all substantially the same or need not be different from one another.

Figure 15:
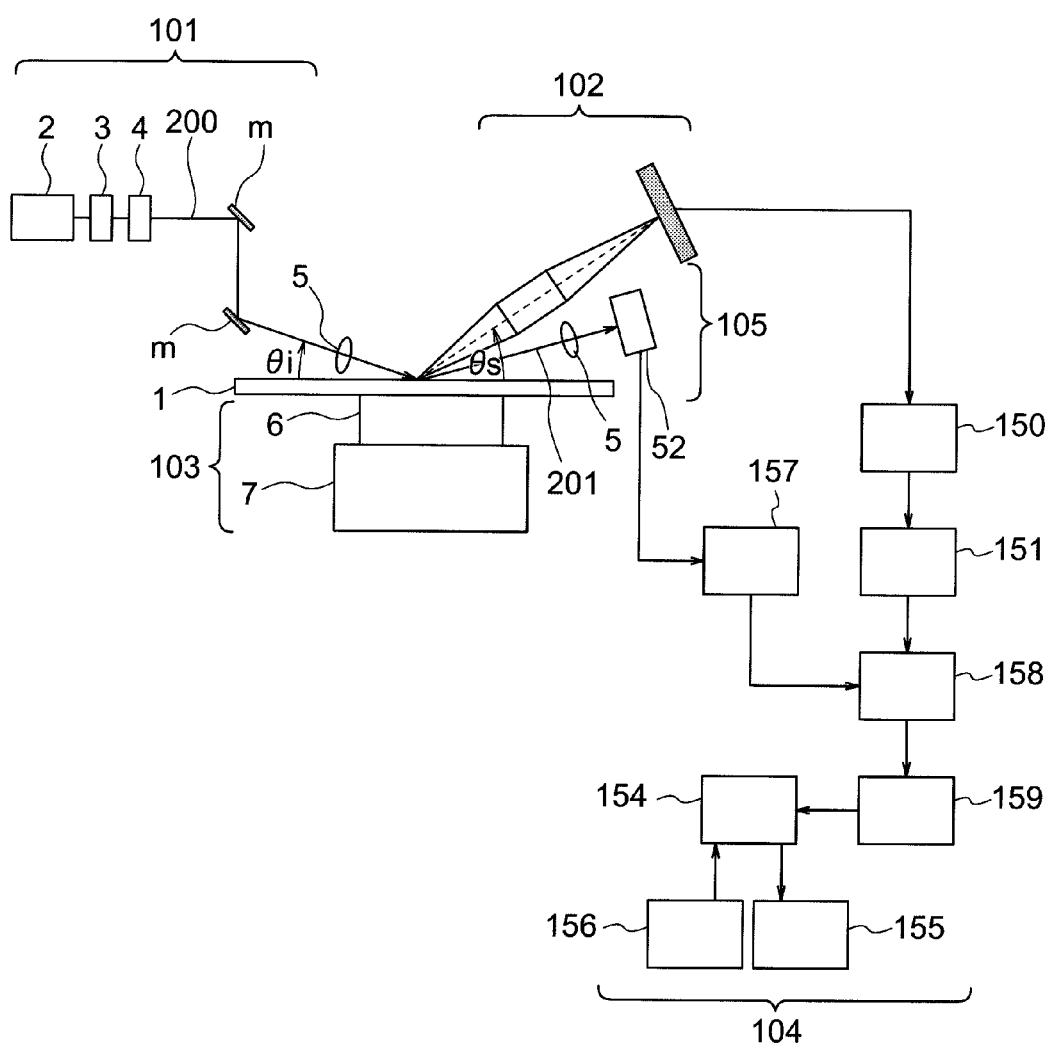
FIG. 15 is a view of a second embodiment of a defect inspection device according to the invention.

A second embodiment of the invention will be described with reference to FIG. 15. In FIG. 15, an illumination optical system 101, a detection optical system 102, a sample stage 103, a signal processing portion 104 and a regularly reflected light observation optical system 105 are provided. The illumination optical system 101 is constituted by a laser light source 2, a beam expander 3, a polarizing element 4, and a condensing lens 5. The beam diameter of a laser beam 200 emitted from the laser light source 2 is adjusted to a desired diameter by the beam expander 3. The laser beam 200 is then converted into a desired polarized state by the polarizing element 4 and an inspection-target region of a sample 1 is illuminated with the laser beam 200 by the condensing lens 5 through reflection mirrors m.

On this occasion, a laser light source which oscillates a visible, ultraviolet or vacuum ultraviolet laser beam may be used as the laser light source 2. An illumination elevation angle $\theta i$ of the oblique illumination optical system 101 is 10 degrees with respect to the wafer surface.

The beam expander 3 is an anamorphic optical system constituted by a plurality of prisms. The beam diameter is changed in only one direction in a plane perpendicular to the optical axis, so that spot illumination or linear illumination is applied on the wafer 1 by use of the condensing lens 5.

The detailed configuration of the detection optical system 102 is substantially the same as that shown in FIG. 3. The detection optical system 102 is constituted by an objective lens 10, a polarizing element 11, an image-forming lens 12, and a line sensor 13. An image of scattered light generated from an illumination region 20 is formed on each pixel of the line sensor 13.

The detection optical system 102 is arranged in the direction of an elevation angle $\theta s$. Detection is performed at the detection elevation angle $\theta s$ which is 30 degrees with respect to the wafer surface. The numerical aperture is 0.3.

The sample stage 103 is constituted by a chuck (not shown) for holding the sample 1, a Z stage (not shown) for performing height control, a rotation stage 6 for rotating the sample, and a translation stage 7 for moving the sample 1 in an R direction.

The sample stage performs rotational scanning and translational scanning to thereby scan the illumination region 20 so that the whole surface of the sample 1 is illuminated spirally.

The signal processing portion 104 has an analog circuit 150, an A/D conversion portion 151, a pixel displacement detection portion 157, a coordinate correction portion 158, a signal addition/defect determination portion 159, a CPU 154, a map output portion 155, and an input portion 156.

The line sensor 13 generates an electric signal in accordance with the quantity of received light. The electric signal is led into the analog circuit 150. In the analog circuit 150, the electric signal is separated into a defect signal and a Haze signal by a high-pass filter or a low-pass filter, and converted into digital signals at a sampling pitch of the order of MHz or higher by the A/D conversion portion 151.

The regularly reflected light observation optical system 105 is disposed in a direction of movement of regularly reflected light 201 and has a condensing lens 5 and a PSD (sensor) 52 (Position Sensitive Detector). S3932 etc. made by Hamamatsu Photonics K.K. may be used as the PSD (sensor) 52.

The second embodiment is characterized in that the magnitude and direction of position displacement of the regularly reflected light 201 are detected by the regularly reflected light observation optical system 105 to thereby detect change in sample height, the magnitude and direction of pixel displacement are calculated based on the magnitude and direction of change in sample height by the pixel displacement detection portion 157, and coordinate correction is performed by the coordinate correction portion 158.

Figure 16:
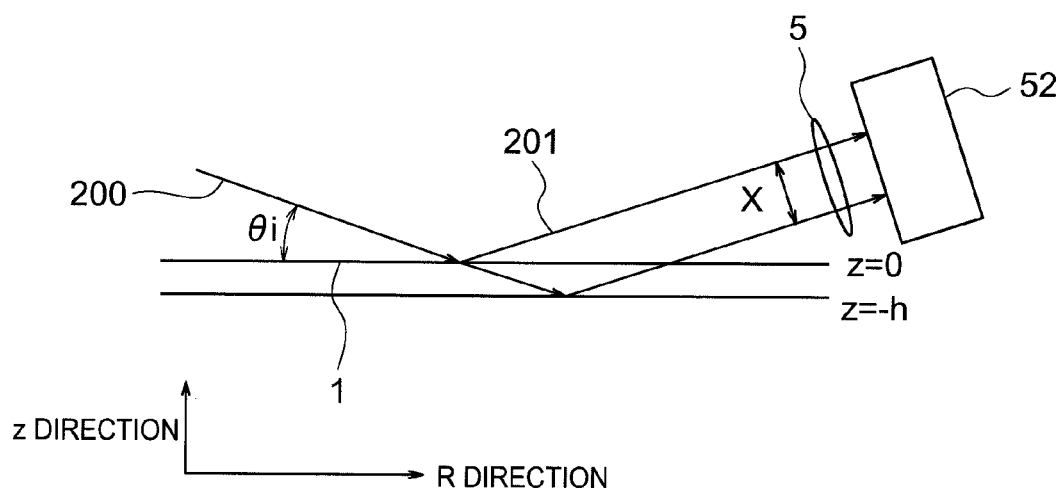
FIG. 16 is a view for explaining a sensor in the second embodiment.

FIG. 16 is an enlarged view of a side of a region where the laser beam 200 in FIG. 15 is incident on the sample 1 at an elevation angle $\theta i$ and regularly reflected light 201 of the laser beam 200 is incident on the PSD (sensor) 52. FIG. 16 shows the case where the surface height of the sample changes by $z=-h$ μm. When the sample height changes as shown in FIG. 16, the position of the regularly reflected light incident on the PSD (sensor) 52 changes. An electric signal corresponding to the incidence position is outputted from the PSD (sensor) 52. Accordingly, displacement of the position of incidence of the regularly reflected light due to change in sample height can be detected while the position of incidence of the regularly reflected light 201 at the position of the sample surface height $z=0$ is used as a reference. When X is the magnitude of displacement in regularly reflected light detection position outputted from the PSD (sensor) 52, X has the relation as follows.

$$X = 2 \cdot h \cdot \cos \theta i \qquad \text{(Expression 1)}$$

When the magnitude X of displacement of the detection position of the regularly reflected light 201 from the sample 1 is detected by the regularly reflected light observation optical system 105 and the (Expression 1) is used, the magnitude h and direction (upward or downward) of change in sample height can be calculated.

The magnitude and direction of change in sample height detected by the aforementioned regularly reflected light observation optical system 105 are inputted to the pixel displacement detection portion 157. The magnitude and direction of pixel displacement can be calculated geometrically based on trigonometric functions by use of three parameters, that is, the azimuth angle direction $\phi$ and the elevation angle direction $\theta s$ in which each detection optical system is disposed, and the magnitude h of change in sample height. The magnitude P of pixel displacement is represented as follows.

$$P = h \cdot \sin \theta s / \tan \phi \qquad \text{(Expression 2)}$$

In the pixel displacement detection portion 157, the magnitude and direction of pixel displacement are calculated in accordance with each detection optical system based on the parameters of the azimuth angle $\phi$, the elevation angle $\theta s$ and the magnitude h of change in sample height based on the (Expression 2), so that a coordinate correction signal is generated and outputted to the coordinate correction portion 158.

A specific example of the coordinate correction signal will be described below. Assume that a coordinate system has two axes (R, $\theta$). Consider the case where change in sample height occurs at $\theta=\theta_0$ (arbitrary constant) and occurrence of pixel displacement of "+5 µm in the R direction" is detected by the aforementioned method. The coordinate correction signal in this case is as follows. As for detection signals of all pixels in the detection optical system 102b, the R-direction coordinate in coordinates at $\theta=\theta_0$ is corrected only by "−5 µm".

The defect signal and the Haze signal are inputted from the A/D conversion portion 151 to the coordinate correction portion 158 and the coordinate correction signal is inputted from the pixel displacement detection portion 157 to the coordinate correction portion 158. Coordinates of each of the defect signal and the Haze signal are corrected based on the coordinate correction signal. The coordinate-corrected signals are led into the signal addition/defect determination portion 159. Contents of processing in the signal addition/defect determination portion 159 will be described below.

Figure 17:
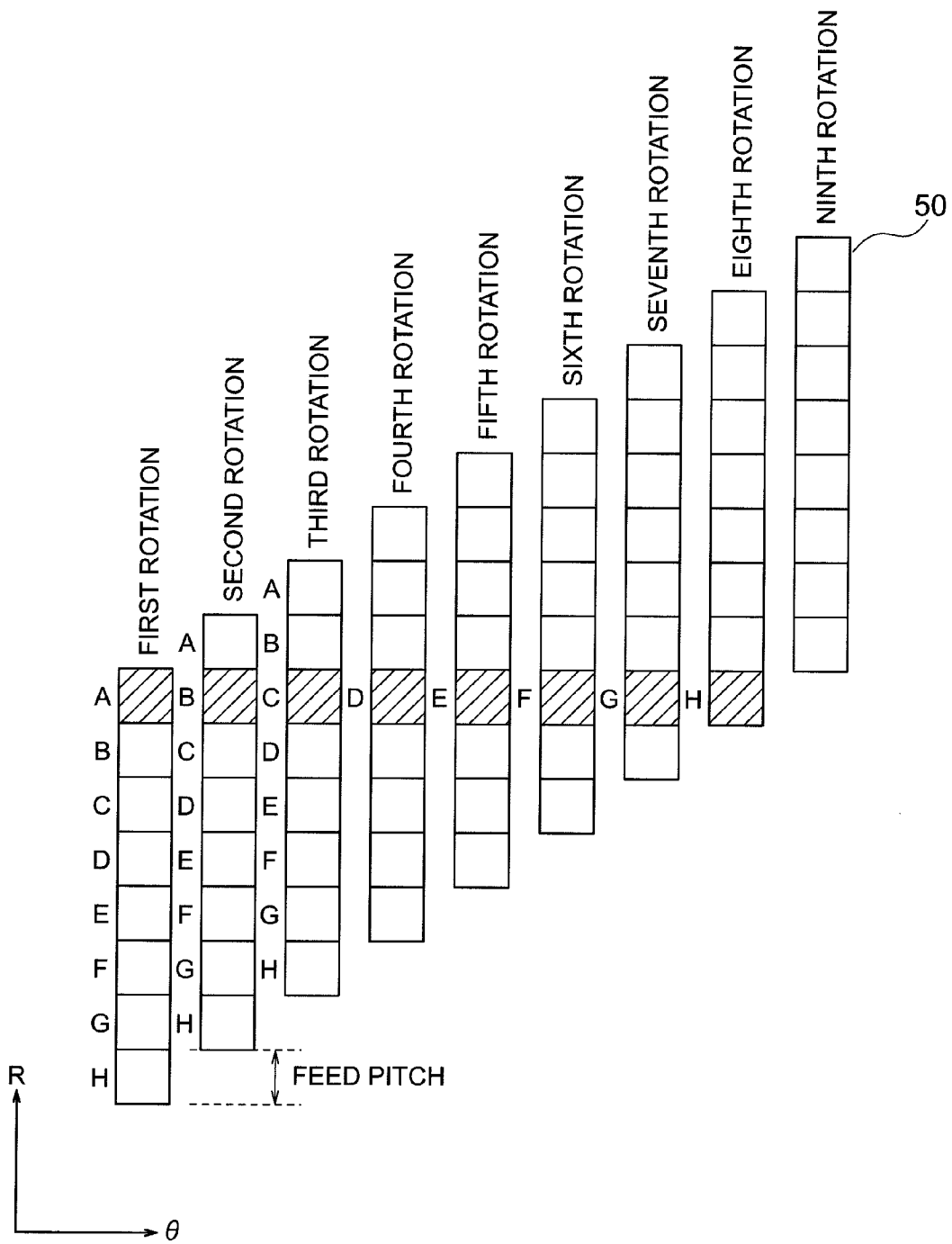
FIG. 17 is a view showing the relation between the detection range of a line sensor and the feed pitch.
Figure 18:
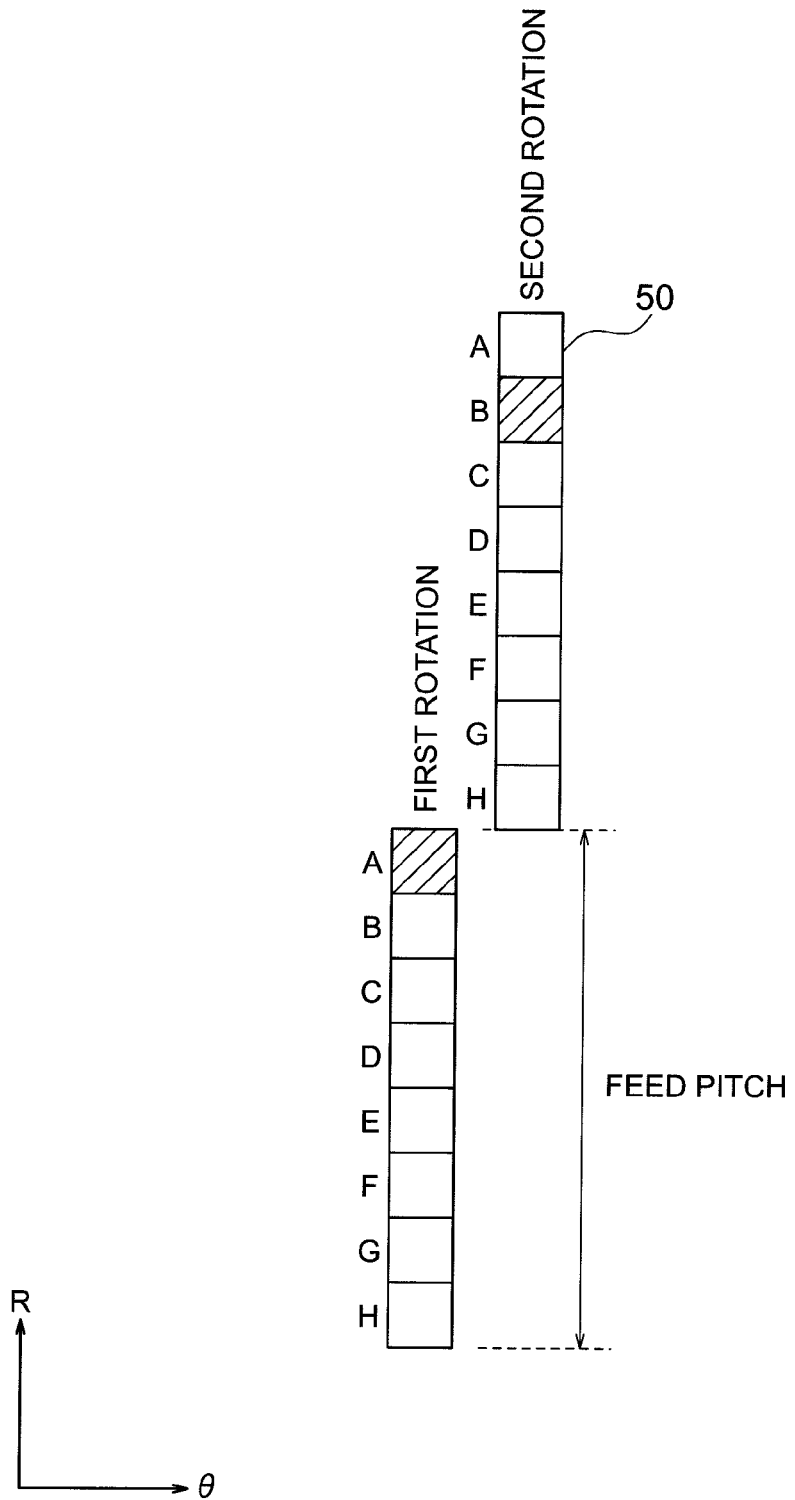
FIG. 18 is a view showing the relation between the detection range of a line sensor and the feed pitch.

In the invention, detection regions are inspected so as to overlap one another and scattered light signals from one and the same region are added up so that S/N can be improved. On this occasion, the distance of radial movement in accordance with one rotation of the sample is called feed pitch. By changing the feed pitch, detection sensitivity and inspection speed can be controlled and description will be made with reference to FIG. 17. FIG. 17 shows the detection position of the line sensor 13 on the sample surface with one detection system used as a subject. The case where a line sensor having eight pixels is used is assumed here. Pay attention to a region detected by a pixel A in the first rotation. When the feed pitch is set to be equal to the size of one pixel, scattered light substantially from one and the same region is detected by an adjacent pixel B in the second rotation. Thereafter, scattered light substantially from one and the same region is detected by each pixel C→D→E→F→G→H whenever one rotation is made. When these signals substantially from one and the same region are added up, S/N can be improved. When the size of the feed pitch is set to be equal to the size of eight pixels as shown in FIG. 18, the area which can be inspected per unit time can be increased to eight times compared with FIG. 17 so that the inspection speed can be shortened. However, the case where defect scattered light is detected by two pixels may occur (pixel cracking). In this case, the quantity of detection light is lowered so that S/N is lowered. It is impossible to avoid this entirely as long as the feed pitch is an integer multiple of the pixel size.

In the second embodiment, scanning is performed in the condition that the feed pitch is shifted from an integer multiple of the number of pixels, and signals of pixels in a common portion of the detection region are added up in the signal addition/defect determination portion 159 to thereby make it possible to suppress lowering of S/N caused by pixel cracking. Description will be made below.

Figure 19:
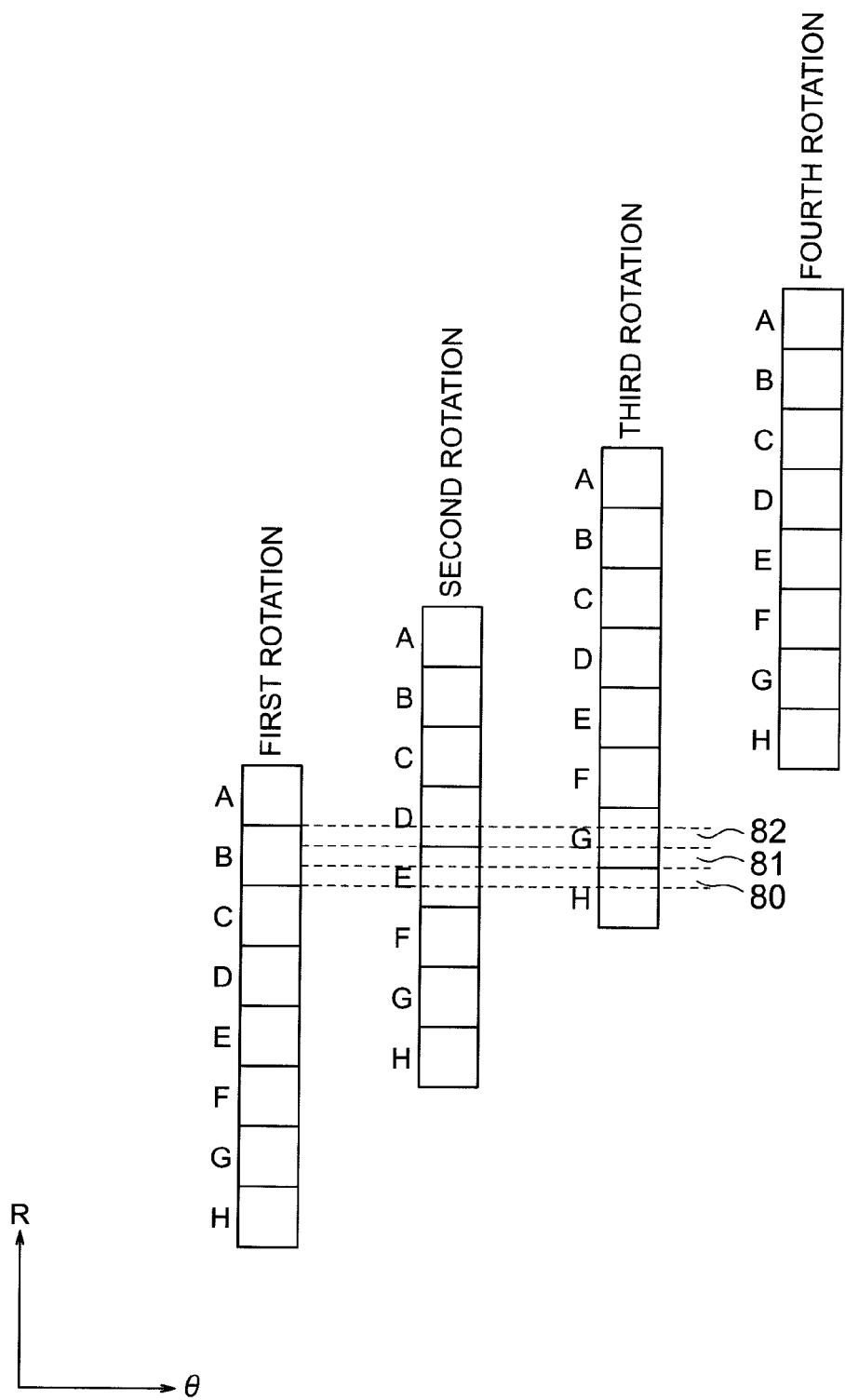
FIG. 19 is a view for explaining sub-pixel addition.

In FIG. 19, it is assumed that a line sensor having eight pixels is used. The feed pitch has a size of 8/3 pixels. The R-direction pixel size on the sample surface is 5 µm.

Pay attention to a region on the sample surface detected by the pixel B in the first rotation. Because the feed pitch is not an integer multiple of the pixel size, there is no combination of pixels in which detection regions entirely coincide with each other. It is known that detection is made by the pixels D and E in the second rotation and detection is made by the pixels G and H in the third rotation. In this case, signal outputs of a region detected by the respective pixels may be subjected to addition processing as follows.

(a) An output of a region detected by the pixel B in the first rotation+an output of a region detected by the pixel E in the second rotation+an output of a region detected by the pixel H in the third rotation→detection signal in a region 80

(b) An output of a region detected by the pixel B in the first rotation+an output of a region detected by the pixel E in the second rotation+an output of a region detected by the pixel G in the third rotation→detection signal in a region 81

(c) An output of a region detected by the pixel B in the first rotation+an output of a region detected by the pixel D in the second rotation+an output of a region detected by the pixel G in the third rotation→detection signal in a region 82

A process of performing scanning in the condition that the feed pitch is shifted from an integer multiple of the pixel size, and applying integration processing to signals of pixels in which a common portion of the detection region is present is hereinafter referred to as sub-pixel addition.

The reason why sub-pixel addition can suppress lowering of S/N caused by pixel cracking is as follows. The case where pixel cracking of defect scattered light between the pixels D and E occurs in the second rotation in FIG. 19 is conceived. However, defect scattered light can be supplemented by the pixel B in the first rotation and defect scattered light can be supplemented by the pixel G in the third rotation, so that pixel cracking can be avoided in the first and third rotations. Consequently, the case where pixel cracking always occurs can be avoided so that lowering of S/N can be suppressed.

Figure 20:
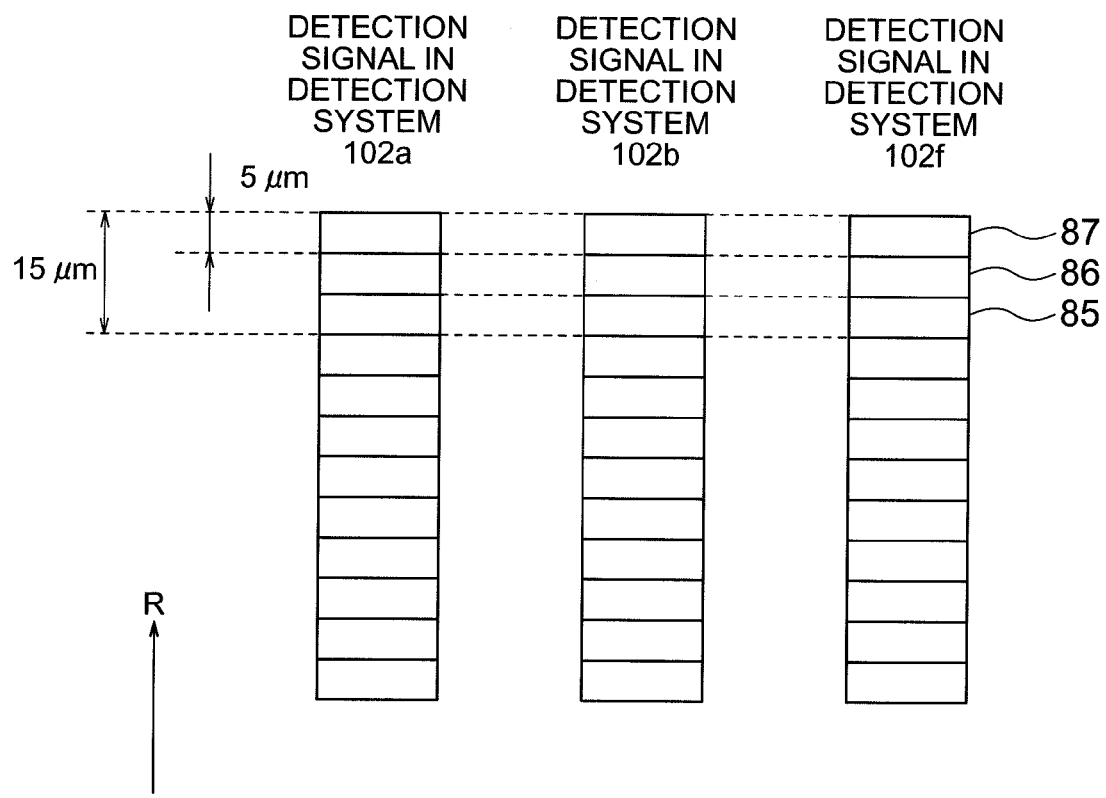
FIG. 20 is a view for explaining sub-pixel addition.

As described above, sub-pixel addition is performed in accordance with each detector, and signals substantially from one and the same coordinates in signals of respective detectors are then subjected to addition processing. Description thereof will be made with reference to FIG. 20. FIG. 20 shows a group of detection signals substantially from one and the same region after detection signals of detection optical systems 102a, 102b and 102f are subjected to sub-pixel addition (in the case where the feed pitch is equal to 8/3 pixels).

Although the original pixel size on the sample surface in each detection system is 15 µm, coordinate accuracy of a resolution not larger than the pixel size can be obtained by sub-pixel addition. When the feed pitch is equal to 8/3 pixels, a pixel size of 5 µm can be obtained. In the detection systems 102a, 102b and 102f, detection signals of a region 85 are added up so that a final detection signal in the region 85 can be obtained. The same rule can be applied to regions 86 and 87. Signals of respective detectors are added up so that final detection signals in the regions 86 and 87 can be obtained. The same rule can be applied to detection signals in other regions. Signals of corresponding regions are added up so that a final detection signal can be obtained.

Defect determination, defect classification and defect size calculation due to threshold processing and Haze processing due to level determination are performed based on the sum signal.

Then, the defect map 160 and the Haze map 161 shown in FIG. 12 are displayed by the map output portion 155 through the CPU 154. The defect map 160 is displayed based on defect type, defect size and detection coordinates fetched at inspection time. The Haze map 161 is displayed based on Haze signal level and detection coordinates fetched at inspection time. The input portion 156 includes a user interface through which a user can perform recipe setting etc.

Figure 21:
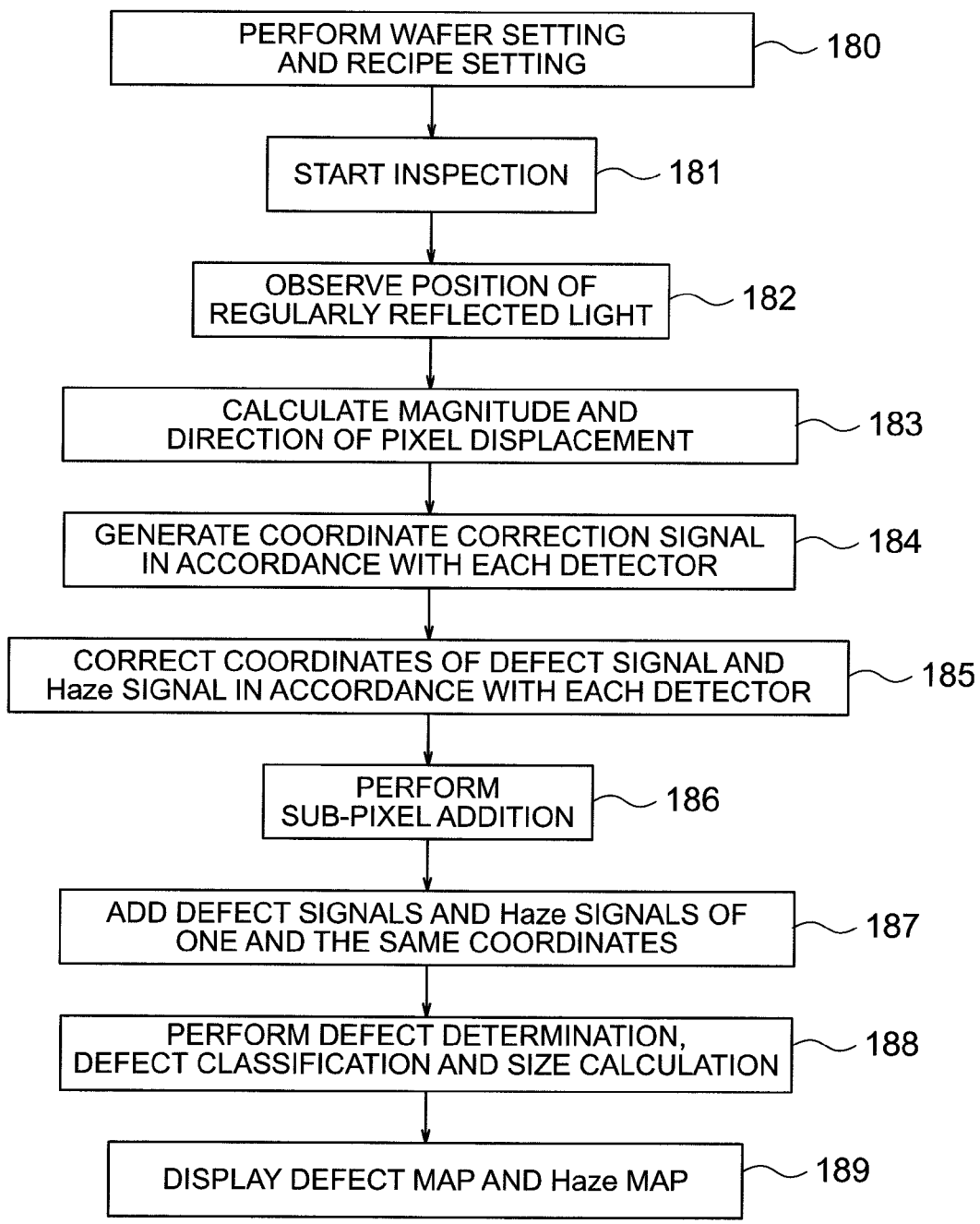
FIG. 21 is a flow of inspection in the second embodiment.

A flow of defect detection processing will be described below with reference to FIG. 21.

First, a sample 1 is set on the stage and an inspection recipe is set (step 180). Inspection is started, and a defect signal and a Haze signal are detected (step 181). The position of regularly reflected light is observed by the regularly reflected light observation optical system 105 to thereby detect the magnitude and direction of change in sample height (step 182). The magnitude and direction of pixel displacement according to each detector are calculated by the pixel displacement detection portion 157 based on the magnitude and direction of change in sample height detected in the step 182 (step 183). A coordinate correction signal according to each detector is generated based on the signal calculated in the step 183 (step 184). In the coordinate correction portion 158, coordinates of the defect signal and the Haze signal are corrected based on the coordinate correction signal (step 185). Sub-pixel addition according to each detector is performed in the signal addition/defect determination portion 159 (step 186). With respect to signals of respective detectors subjected to sub-pixel addition, signals from one and the same coordinates are added up (step 187). Defect determination, defect classification, size calculation and Haze processing are performed based on the sum signal (step 188), so that the defect map and the Haze map are displayed (step 189).

Although description has been made with reference to FIG. 15 in the case where only one detection optical system is located in addition to oblique illumination for performing illumination at a low elevation angle θi by way of example, a perpendicular illumination optical system for illuminating the sample substantially in a perpendicular direction may be provided.

Although description has been made in the case where only one detection optical system 102 disposed at a detection elevation angle θs is located by way of example, a plurality of detection optical systems may be disposed in directions of elevation angles. The sizes of elevation angles and the sizes of numerical apertures in the detection optical systems provided thus are not limited.

A plurality of detection optical systems 102 are located at different azimuth angle directions φ as shown in FIG. 1. Elevation angles at which these detection optical systems 102 are disposed need not be all substantially the same or need not be different from one another. The azimuth angles of arrangement of the detection optical systems 102 are not limited likewise.

Although an example in which S3932 made by Hamamatsu Photonics K.K. is used as the PSD 52 has been described, the model type of the PSD used is not limited.

Although description has been made with reference to FIG. 19 in the case where the feed pitch is equal to 8/3 pixels by way of example, any feed pitch may be used as long as the feed pitch is not an integer multiple of the pixel. The number of pixels and the pixel size are not limited.

Although description has been made with reference to FIG. 20 in the case where three detection systems are used by way of example, signals substantially from one and the same region in all detection systems provided thus are subjected to signal addition.

As described above, in accordance with the embodiments of the invention, detection signals of adjacent pixels are subjected to integration processing, so that scattered light generated substantially from one and the same region can be added up even in the case where pixel displacement occurs.

Moreover, scanning is performed in the condition that the feed pitch is shifted from an integer multiple of the pixel, and regularly reflected light of the laser beam irradiated on the sample is monitored to thereby detect the magnitude and direction of change in sample height, correct the coordinates of the detection signal based on the signal and perform sub-pixel addition so that scattered light signals generated substantially from one and the same region can be added up accurately.

REFERENCE SIGNS LIST 1 sample, 2 laser light source, 3 beam expander, 4 polarizing element, m mirror, 5 condensing lens, 6 rotation stage, 7 translation stage, 10 objective lens, 11 polarizing element, 12 image-forming lens, 1330 to 32 line sensor, 1516 image surface, 20, 20', 20" illumination region, 1721A, 21B detection range of the line sensor on the sample surface, 25, 26, 27 direction of movement of the illumination region due to change in sample height, 33 defect scattered light, 40 PSD, 50 detection range of the line sensor on the sample surface, 80 to 82, 85 to 87 detection region, 101 illumination optical system, 102, 102a to 102H detection optical system, 103 sample stage, 104 signal processing portion, 105 regularly reflected light observation optical system, 150 analog circuit, 151 A/D conversion portion, 152 adjacent pixel integration portion, 153, 159 signal addition/defect determination portion, 154 CPU, 155 map output portion, 156 input portion, 157 pixel displacement detection portion, 158 coordinate correction portion, 160 defect map, 161 Haze map, 170 to 176, 180 to 189 inspection flow, 200 laser beam, 201 regularly reflected light, 210 longitudinal direction of illumination, 212 optical axis of the detection optical system, 213 direction of arrangement of pixels in the line sensor

The invention claimed is:

1. A defect inspection method comprising the steps of:
    irradiating a predetermined region of an inspection target with illumination light by an illumination optical system;
    detecting a plurality of scattered lights scattered from the predetermined region of the inspection target illuminated by the illumination step, by a detection optical system having a plurality of detectors each provided with a plurality of pixels by which the scattered light can be detected in a manner that the plurality of detectors detect the scattered light in different azimuth angle directions with respect to the surface of the inspection target, respectively;
    adding up a plurality of detection signals based on the plurality of scattered lights detected by the detection step with respect to the plurality of scattered lights substantially from one and the same region of the inspection target to thereby determine a defect on the surface of the inspection target; and
    translationally moving the inspection target by a pitch of a size different from an integer multiple of a pixel number of one pixel in the plurality of detectors.

2. The defect inspection method according to claim 1, wherein the adding step performs addition processing while shifting the pixels of the plurality of detection signals by intervals of (1/a size of pixels in the detector)×(the pitch).

3. The defect inspection method according to claim 1, wherein the detection step detects scattered light from the predetermined region of the inspection target due to illumination light of the illumination optical system by a line sensor.

4. A defect inspection device:
    an illumination optical system configured to irradiate a predetermined region of an inspection target with illumination light;

a detection optical system configured to detect a plurality of scattered lights scattered from the predetermined region of the inspection target illuminated by the illumination optical system, the detection optical system having a plurality of detectors each provided with a plurality of pixels by which the scattered light can be detected in a manner that the plurality of detectors detect the scattered light in different azimuth angle directions with respect to the surface of the inspection target, respectively;

a signal addition/defect determination system configured to add up a plurality of detection signals based on the plurality of scattered lights detected by the detection optical system with respect to the plurality of scattered lights substantially from one and the same region of the inspection target to thereby determine a defect on the surface of the inspection target; and the signal addition/defect determination system configured to translationally move the inspection target by a pitch of a size different from an integer multiple of a pixel number of one pixel in the plurality of detectors.

5. The defect inspection device according to claim 4, wherein the signal addition/defect determination system further configured to perform addition processing while shifting the pixels of the plurality of detection signals by intervals of (1/a size of pixels in the detector)×(the pitch).

6. The defect inspection device according to claim 4, wherein the detection optical system configured to detect scattered light from the predetermined region of the inspection target due to illumination light of the illumination optical system by a line sensor.

* * * * *